US00PP13462P2

(12) United States Plant Patent
Vandenberg

(10) Patent No.: US PP13,462 P2
(45) Date of Patent: Jan. 7, 2003

(54) CHRYSANTHEMUM PLANT NAMED 'DASH'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 15 days.

(21) Appl. No.: 09/899,981

(22) Filed: Jul. 9, 2001

(51) Int. Cl.[7] ..... A01H 5/00
(52) U.S. Cl. ..... Plt./295

(58) Field of Search ..... Plt./286, 295

*Primary Examiner*—Howard J. Locker
(74) *Attorney, Agent, or Firm*—C. A. Whealy

(57) ABSTRACT

A distinct cultivar of Chrysanthemum plant named 'Dash', characterized by its small anemone-type inflorescences that are about 3.7 cm in diameter; attractive golden yellow-colored ray and disc florets; response time about 68 days; freely flowering habit; dark green foliage; dark purple-colored stems; and excellent postproduction longevity with inflorescences maintaining good substance and color for about three weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Dash'.

The new Chrysanthemum is a product of a planned breeding program conducted by the Inventor in Salinas, Calif. and Alva, Fla. The objective of the breeding program is to create new cut Chrysanthemum cultivars having inflorescences with desirable colors and good form and substance.

The new Chrysanthemum originated from a cross made by the Inventor in September, 1997, in Salinas, Calif., of a proprietary Chrysanthemum seedling selection identified as code number K548, not patented, as the female, or seed, parent with a proprietary Chrysanthemum seedling selection identified as H049, not patented, as the male, or pollen, parent.

The cultivar Dash was discovered and selected by the Inventor as a flowering plant within the progeny of the stated cross in a controlled environment in Alva, Fla., in November, 1998. The selection of this plant was based on its desirable inflorescence color and good form and substance.

Asexual reproduction of the new Chrysanthemum by terminal cuttings taken in a controlled environment in Alva, Fla. since February, 1999, has shown that the unique features of this new Chrysanthemum are stable and reproduced true to type in successive generations.

SUMMARY OF THE INVENTION

Plants of the cultivar Dash have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dash'. These characteristics in combination distinguish 'Dash' as a new and distinct cultivar:

1. Upright cut Chrysanthemum that is usually grown as a natural spray.

2. Freely flowering habit, about 8 inflorescences per flowering stem.
3. Small anemone-type inflorescences that are about 3.7 cm in diameter.
4. Attractive golden yellow-colored ray and disc florets.
5. Response time about 68 days.
6. Dark green foliage.
7. Dark purple-colored stems.
8. Excellent postproduction longevity with inflorescences maintaining good substance and color for about three weeks in an interior environment.

Plants of the female parent, the seedling selection identified as code number K548, and plants of the new Chrysanthemum differ in inflorescence form and color as plants of the female parent have daisy-type inflorescences with dark pink-colored ray florets.

Plants of the male parent, the seedling selection identified as code number H049, and plants of the new Chrysanthemum differ primarily in inflorescence color as ray florets of the male parent are white in color.

Plants of the new Chrysanthemum can be compared to plants of the cultivar Fargo, disclosed in U.S. Plant Pat. No. 9,108. In side-by-side comparisons conducted by the Inventor in Madrid, Cundinamarca, Colombia, South America, plants of the new Chrysanthemum are more vigorous than plants of the cultivar Fargo. In addition, plants of the cultivar Fargo have daisy-type inflorescences whereas plants of the new Chrysanthemum have anemone-type inflorescences.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Dash' grown as a natural spray.

The photograph on the second sheet comprises a close-up view of a typical flowering stem of 'Dash' grown as a natural spray.

DETAILED BOTANICAL DESCRIPTION

In the following description, color references are made to The Royal Horticultural Society Colour Chart except where general terms of ordinary dictionary significance are used. The aforementioned photographs and following observations and measurements describe plants grown in Madrid, Cundinamarca, Colombia, South America, under conditions which approximate commercial practice in a single-layer polyethylene-covered greenhouse. Two-week old rooted cuttings were planted on Nov. 30, 2000 and received 14 long day/short nights followed by short day/long nights until flowering. Plants were grown as single-stem natural spray cut Chrysanthemums. During the production time, the following environmental conditions were measured: day temperatures, 19 to 24° C.; night temperatures, 4 to 12° C.; and light levels, 3,000 to 5,000 foot-candles. Measurements and numerical values represent averages for six to ten typical flowering stems and were taken about 9 to 10 weeks after the start of short days.

Botanical classification: *Chrysanthemum×morifolium* cultivar Dash.

Commercial classification: Anemone-type cut Chrysanthemum,

Parentage:

*Female or seed parent*.—Proprietary *Chrysanthemum× morifolium* seedling selection identified as code number K548, not patented.

*Male or pollen parent*.—Proprietary *Chrysanthemum× morifolium* seedling selection identified as code number H049, not patented.

Propagation:

*Type*.—Terminal tip cuttings.

*Time to rooting*.—About 10 to 14 days with soil temperatures of 18 to 21° C.

*Root description*.—Fine, fibrous and well-branched.

Plant description:

*Appearance*.—Herbaceous anemone-type cut flower that is typically grown as a natural spray.

*Flowering stem description*.—Aspect: Erect. Length; About 105 cm. Diameter (natural spray diameter): About 9.5 cm. Diameter (base of stem): About 5 mm. Internode length: About 4.6 cm. Texture: Densely pubescent; longitudinally ridged. Color: 146A overlain with 187A.

*Foliage description*.—Arrangement: Alternate. Length: About 7.25 cm. Width: About 4.7 cm. Apex: Cuspidate. Base: Attenuate. Margin: Palmately lobed; sinuses divergent. Texture: Upper and lower surfaces pubescent; smooth and leathery; veins prominent on lower surface. Color: Young foliage upper surface: Darker than 147A. Young foliage lower surface: Darker than 147B. Mature foliage upper surface: 147A. Mature foliage lower surface: Close to 147B. Venation, upper surface: 147A to 147B. Venation, lower surface: 147B. Petiole: Length: About 1.75 cm. Diameter: About 3 mm. Color: Upper surface: 147B. Lower surface: 147B to 146B.

Flowering description:

*Appearance*.—Anemone-type inflorescence form with elongated oblong-shaped ray florets and large central disc. Inflorescences borne on terminals, arising from leaf axils. Disc and ray florets arranged acropetally on a capitulum.

*Flowering response*.—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 68 days later when grown as a natural spray.

*Postproduction longevity*.—In an interior environment, flowering stems will maintain good color and substance for about three weeks in an interior environment after one week of cool storage.

*Quantity of inflorescences*.—Freely flowering habit, about 8 inflorescences per stem develop.

*Inflorescence size*.—Diameter: About 3.7 cm. Depth (height): About 1.8 cm. Diameter of disc: About 2.1 cm. Diameter of receptacle: About 5 mm.

*Inflorescence buds*.—Shape: Flattened sphere. Height: About 6 mm. Diameter: About 8 mm. Color: 137A.

*Ray florets*.—Shape: Elongated oblong; slightly reflexed. Length: About 1.8 cm. Width: About 5.5 mm. Corolla tube length: About 6 mm. Apex: Emarginate. Base: Fused. Texture: Satiny, smooth, glabrous; slightly longitudinally ridged. Aspect: Initially upright: when mature, perpendicular to peduncle. Number of ray florets per inflorescence: About 68 arranged in three or four rows. Color: When opening, upper and lower surfaces: 12A. Fully opened, upper surface: 12A; color does not fade with subsequent development. Fully opened, lower surface: 12A; towards apex, overtones of close to 53A.

*Disc florets*.—Shape: Tubular, enlarged. Length: About 1.3 cm. Width: Apex: About 3 mm. Base: About 1.5 mm. Number of disc florets per inflorescence: About 107, massed at center of receptacle. Color: Immature: 144A to 144B. Mature, outer surface: Apex: 12A to 13A, apices tipped with closed to 187A. Mid-section: 12A. Base: 144A. Mature, throat: 12A to 13A.

*Peduncles*.—Length: First peduncle: About 8.4 cm. Fourth peduncle: About 10.1 cm. Seventh peduncle: About 12.75 cm. Diameter: About 2.25 mm. Angle: About 35 to 40° from vertical. Strength: Very strong. Texture: Pubescent. Color: 146A slightly overlain with 187A.

*Reproduction organs*.—Androecium: Present on disc florets only. Anther color: Close to 12A. Amount of pollen: None observed. Gynoecium: Present on both ray and disc florets.

*Seed*.—Seed production has not been observed.

Disease/pest resistance: Resistance to pathogens and pests common to Chrysanthemums has not been observed on plants grown under commercial conditions.

Temperature tolerance: Plants of the new Chrysanthemum have demonstrated good tolerance to low temperatures 5° C. Plants of the new Chrysanthemum do not tolerate high temperatures greater than 40° C.

It is claimed:

1. A new and distinct cultivar of Chrysanthemum plant named 'Dash', as illustrated and described.

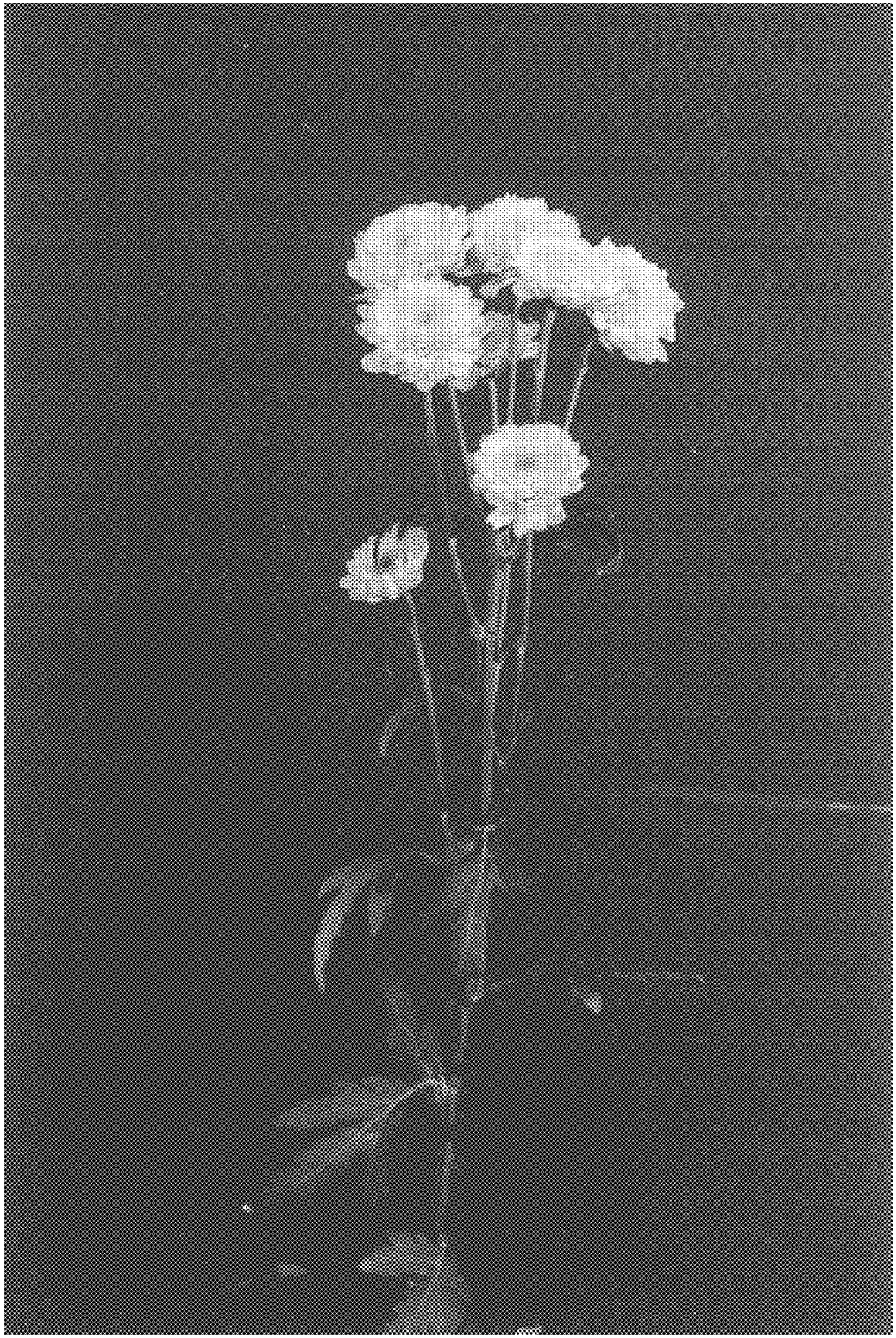

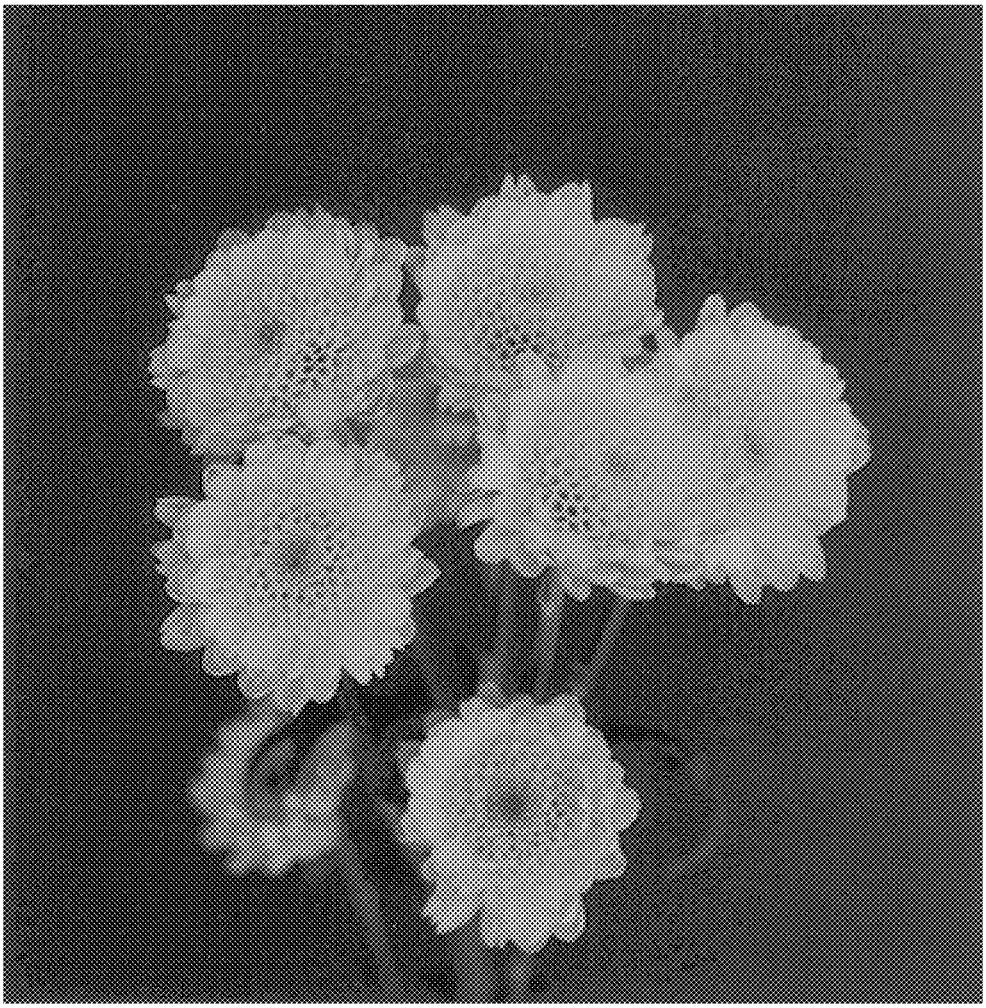

* * * * *